(12) United States Patent
Singer et al.

(10) Patent No.: US 9,527,075 B2
(45) Date of Patent: Dec. 27, 2016

(54) LOW-VOLUME SYRINGE PIPETTE

(71) Applicants: Michael E. Singer, Canton, OH (US); Christine Flick, Streetsboro, OH (US)

(72) Inventors: Michael E. Singer, Canton, OH (US); Christine Flick, Streetsboro, OH (US)

(73) Assignee: Austen BioInnovation Institute in Akron, Akron, OH (US)

( * ) Notice: Subject to any disclaimer, the term of this patent is extended or adjusted under 35 U.S.C. 154(b) by 455 days.

(21) Appl. No.: 14/066,090

(22) Filed: Oct. 29, 2013

(65) Prior Publication Data

US 2014/0123776 A1    May 8, 2014

Related U.S. Application Data

(60) Provisional application No. 61/722,304, filed on Nov. 5, 2012.

(51) Int. Cl.
*B01L 3/02* (2006.01)
*A61M 5/20* (2006.01)
*A61M 5/315* (2006.01)

(52) U.S. Cl.
CPC .............. *B01L 3/021* (2013.01); *A61M 5/204* (2013.01); *A61M 5/31596* (2013.01); *B01L 3/0217* (2013.01); *B01L 2200/0689* (2013.01); *B01L 2300/028* (2013.01); *B01L 2300/0864* (2013.01); *B01L 2400/0633* (2013.01)

(58) Field of Classification Search
None
See application file for complete search history.

(56) References Cited

U.S. PATENT DOCUMENTS

| | | |
|---|---|---|
| 3,985,122 A | 10/1976 | Topham |
| 4,036,064 A | 7/1977 | Hydo |
| 4,679,446 A | 7/1987 | Sheehan et al. |
| 5,511,433 A | 4/1996 | Sabloewski et al. |
| 5,763,278 A | 6/1998 | Sickinger et al. |
| 5,817,955 A * | 10/1998 | Gherson et al. ........... 73/864.35 |
| 6,514,231 B1 | 2/2003 | Szapiro et al. |
| 7,294,309 B1 | 11/2007 | Goldberg et al. |

(Continued)

OTHER PUBLICATIONS

PCT International Search Report and Written Opinion from International Application PCT/US2013/067255, mailed on Jan. 24, 2014, 13 pages.

(Continued)

*Primary Examiner* — Robert R Raevis
(74) *Attorney, Agent, or Firm* — Brouse McDowell; Heather M. Barnes; Michael G. Craig

(57) ABSTRACT

One or more techniques and/or systems are disclosed for an apparatus for use with a syringe or pipette. A chamber body can comprise a first chamber, a second chamber, and a fluid port. A first fluid seal can be disposed in the first chamber, and a second fluid seal can be disposed in the second chamber. The chamber body can comprise a first volume which is defined by a first chamber wall, the first seal, and the second seal, when the first seal and second seal are disposed in a first position. The first volume can also be defined by a sum of: a second volume defined by at least a second chamber wall, the first seal, the second seal; and a third volume comprising fluid displaced at the fluid port, when the first seal and second seal are disposed in a second position.

20 Claims, 12 Drawing Sheets

(56) References Cited

U.S. PATENT DOCUMENTS

| | | |
|---|---|---|
| 7,900,850 B2 | 3/2011 | Zengerle et al. |
| 7,935,078 B2 | 5/2011 | Horita et al. |
| 2002/0108455 A1 | 8/2002 | Suovaniemi et al. |
| 2005/0220676 A1 | 10/2005 | Tran |
| 2007/0048193 A1 | 3/2007 | Wilmer |
| 2009/0088693 A1 | 4/2009 | Carter |
| 2009/0220364 A1* | 9/2009 | Rigal et al. .................. 417/521 |

OTHER PUBLICATIONS

Hamilton Company, 7000 Series Modified Microliter Syringe, Product Data Sheet, Jul. 2007, 3 pages.

Idex Health & Science LLC, Innovadyne Nanodrop Express, Product Data Sheet, 2009, 2 pages.

PCT International Preliminary Report on Patentability, International Application PCT/US2013/067255, mailed on May 14, 2015, 9 pages.

PCT International Search Report and Written Opinion from International Application PCT/US2015/014466, mailed on May 20, 2015, 11 pages.

\* cited by examiner

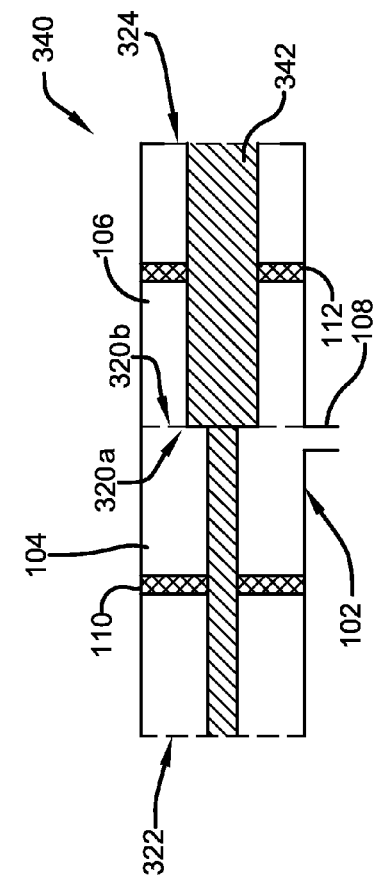
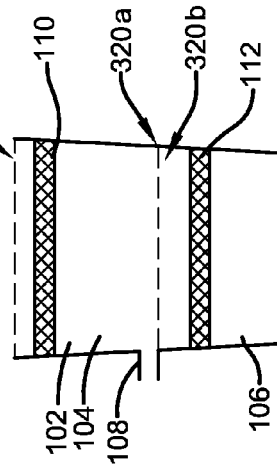
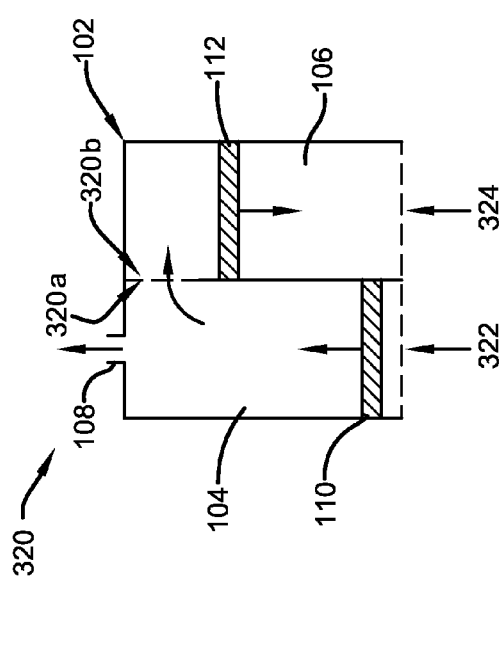
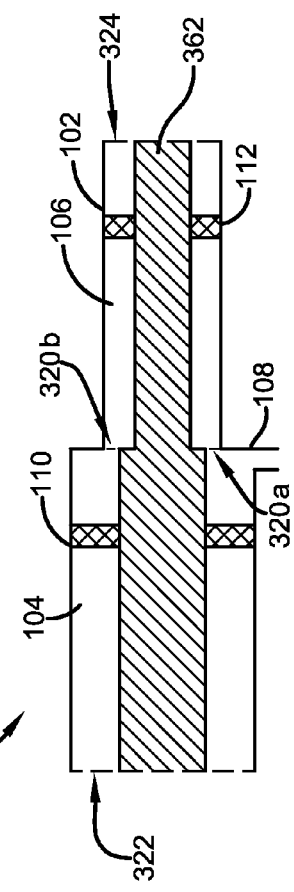
FIGURE 3C
FIGURE 3E
FIGURE 3B
FIGURE 3D

LOW-VOLUME SYRINGE PIPETTE

CROSS-REFERENCE TO RELATED APPLICATIONS

This application claims priority to provisional patent U.S. Ser. No. 61/722,304 entitled ULTRA LOW VOLUME SYRINGE/PIPETTE, filed Nov. 5, 2012, which is incorporated herein by reference.

BACKGROUND

Pipettes and syringes are common tools used in medicine and/or scientific research, for example, for injecting measured amounts of liquid and/or transporting a measured volume of liquid. These tools can be comprised of varying designs, depending on the intended use, for example, having differing volumes and/or levels of precision, for transferring small amounts of liquids or injecting very-low volumes of liquid. Further, they can be made from a variety of materials, including glass, polymers, metals, etc. and can also comprise more complex adjustable or automated pipettes. When drawing a liquid into the device, a partial vacuum may be created above the liquid-holding chamber to draw up, and subsequently inject/dispense the liquid.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

As provided herein, one or more devices and techniques for use with a syringe or pipette that may provide improved resolution in drawing and dispensing liquids. For example, typical syringes or pipettes utilize a one to one ratio when operating the actuator/plunger to draw or dispense liquids. As an example, a syringe or pipette may be configured to draw or dispense a low volume while the actuator/plunger translates in a manner that is typical for a much larger volume. In this way, for example, the user can operate the device in a typical manner while merely dispensing a low volume of liquid, thereby providing greater granularity in dispensing from the device.

In one implementation, an apparatus for use with a syringe or pipette can comprise a chamber body that comprises a first chamber, a second chamber, and a fluid port. Further, a first seal can be disposed in the first chamber, and a second seal can be disposed in the second chamber. Additionally, the chamber body can comprise a first volume that is defined by at least a first chamber wall, the first seal, and the second seal, when the first seal and second seal are disposed in a first position, respectively. The first volume may alternately, or also be, defined by a sum of: a second volume defined by at least a second chamber wall, the first seal, the second seal; and a third volume comprising fluid displaced at the fluid port, when the first seal and second seal are disposed in a second position, respectively.

To the accomplishment of the foregoing and related ends, the following description and annexed drawings set forth certain illustrative aspects and implementations. These are indicative of but a few of the various ways in which one or more aspects may be employed. Other aspects, advantages and novel features of the disclosure will become apparent from the following detailed description when considered in conjunction with the annexed drawings.

BRIEF DESCRIPTION OF THE DRAWINGS

What is disclosed herein may take physical form in certain parts and arrangement of parts, and will be described in detail in this specification and illustrated in the accompanying drawings which form a part hereof and wherein:

FIGS. 3A, 3B, 3C, 3D and 3E are component diagrams illustrating example implementations of an apparatus for use with a syringe or pipette.

DETAILED DESCRIPTION

Figure 1A:
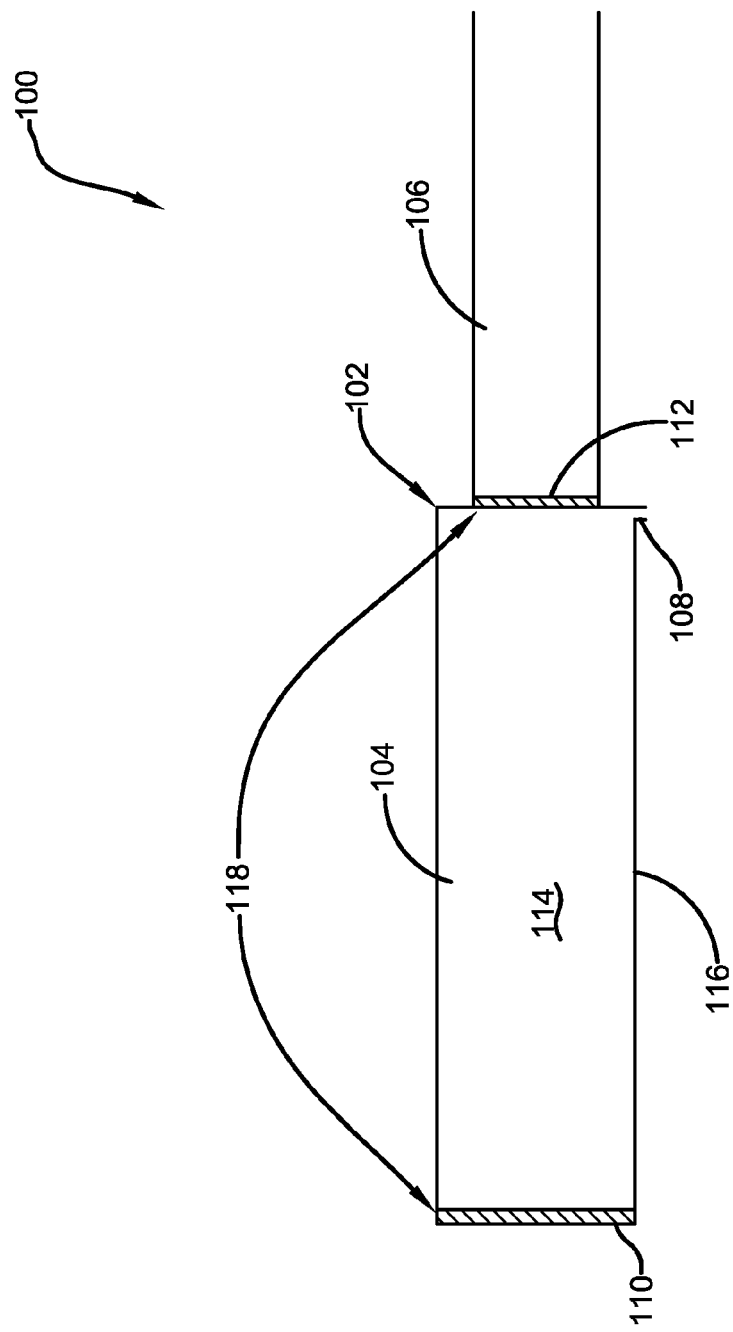
FIGS. 1A and 1B are component diagrams illustrating implementations of an exemplary apparatus for use with a syringe or pipette.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices may be shown in block diagram form in order to facilitate describing the claimed subject matter.

An apparatus may be devised that can be used to transfer a desired volume of fluid, comprising, for example, what may typically be considered to be a low volume (e.g., ultra-low, such as less than a milliliter) of fluid in conjunction with medical and/or scientific research utilization. As one example, a pipette-type application use of the apparatus may utilize chambers comprising different volumes, where the difference in volumes may comprise a volume of fluid displaced by the apparatus (e.g., either into or out-of the pipette). In this example, the displaced volume may comprise a small fraction of the total volume of the chamber. This may allow for a relatively normal use of a coupled actuator (e.g., plunger), while providing fine grained transfer of a fluid. Further, for example, graduation indicators on the pipette, for example, may provide visual identification of the desired low-volume for a user.

Figure 1B:
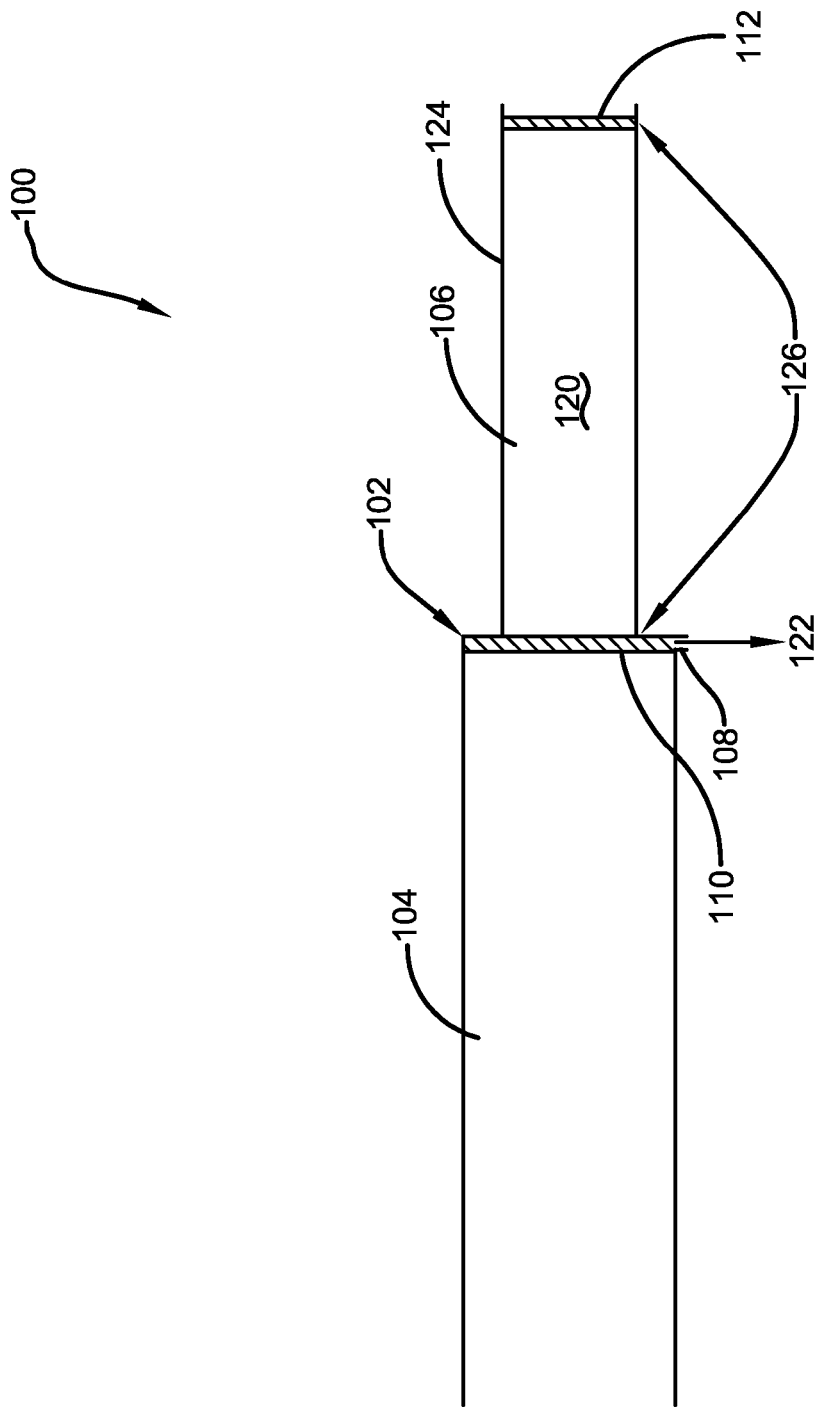

FIGS. 1A and 1B are component diagrams illustrating example implementations of an exemplary apparatus 100 for use with a syringe or pipette. In FIGS. 1A and 1B, the exemplary apparatus 100 comprises a chamber body 102. The chamber body 102 comprises a first chamber 104, a second chamber 106, and a fluid port 108. In one implementation, as illustrated in the exemplary apparatus 100 of FIGS. 1A and 1B, the first chamber 104 and second chamber 106 can be disposed in a sequential arrangement, for example, such that they share a similar central, longitudinal axis. However, the arrangement of the first chamber 104 and second chamber 106 is not limited to this example implementation. In other implementations, the respective chambers may be arranged in a geometrically parallel disposition, for example, such that the respective chambers are coupled side-by-side. As another example, the first chamber (e.g., 104) may be disposed orthogonal to the second chamber (e.g., 106). It is anticipated that those skilled in the art may devise alternate arrangements for the respective chambers implemented in the apparatus used in the pipette or syringe. For example, the chambers may be aligned at a desired angle (e.g., any angle designed for a particular purpose) to each other; and/or the chambers' axes may not be aligned with each other (e.g., the axis may be offset from each other).

In FIG. 1A, the chamber body 102 of the exemplary apparatus 100 comprises a first volume 114. The first volume 114 can be defined by at least a first chamber wall 116, the first seal 110, and the second seal 112, when the first seal 110 and second seal 112 are disposed in a first position 118, respectively. Further, as illustrated in FIG. 1B, the first volume 114 (from FIG. 1A) can be defined by a sum of a second volume 120, which can be defined by at least a second chamber wall 124, the first seal 110, and the second seal 112, and a third volume 122 comprising fluid displaced at the fluid port 108, when the first seal 110 and second seal 112 are disposed in a second position 126, respectively.

As an illustrative example, in FIGS. 1A and 1B, the first volume can be defined differently depending on a position of the first seal 110 and second seal 112 in the chamber body. That is, for example, when the first and second seals 110, 112 are disposed in the first position 118, substantially the entire first volume is disposed in within the first chamber 104. Alternately, when the first and second seals 110, 112 are disposed in the second position 126, the first volume can be divided between the second chamber 106 and the volume displaced at the fluid port 108.

In one implementation, translating the first and second seals 110, 112 between the first position 118 and the second position 126 may effectively force a portion of the first volume 114 to be displaced at the fluid port 108. As an example, a first volume of fluid disposed in the first chamber 104 may be displaced into the second chamber 106 and out of the fluid port 108 when the first and second seals 110, 112 are translated between the first position 118 and the second position 126. That is, in this example, a first fraction of the first volume of fluid can be displaced into the second chamber 106 and a second fraction of the first volume of fluid can be displaced at (e.g., out of) the fluid port 108. It should be noted that the term "fluid" may be representative of any fluid (e.g., liquid, gas, plasma) that is typically indicated by the study of fluid mechanics.

Figure 2:
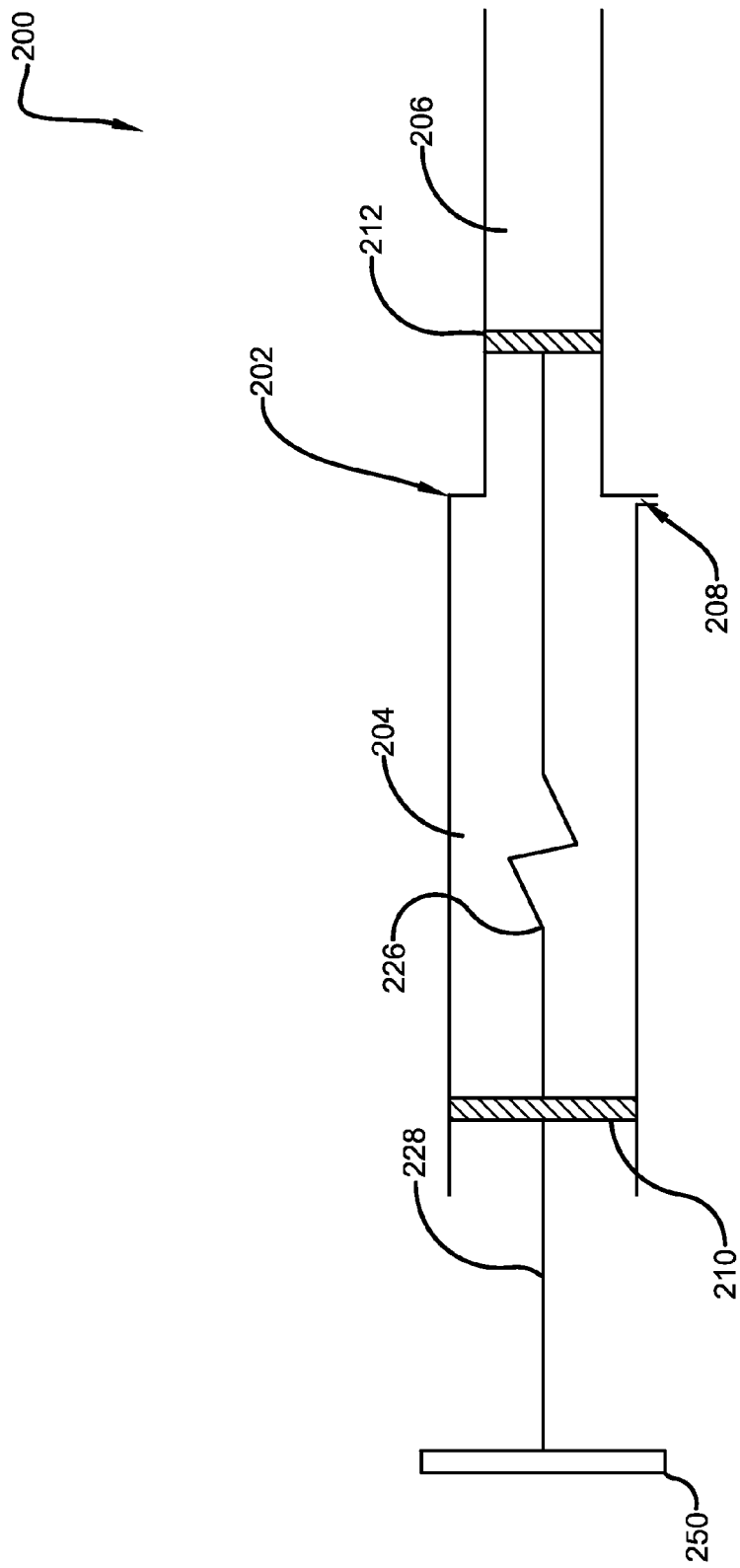
FIG. 2 is a component diagram illustrating an example implementation of an apparatus for use with a syringe or pipette.

FIG. 2 is a component diagram illustrating an example implementation 200 of an apparatus for use with a syringe or pipette. With continued reference to FIGS. 1A, 1B, in one implementation, as illustrated in FIG. 2, a first seal 210 can be operably coupled 226 with a second seal 212, such that the second seal 212 may be translated in a second chamber 206 of a chamber body 202 in proportion to a translation of the first seal 210 in a first chamber 204 of the chamber body. That is, for example, translating the first seal 210 inside the first chamber 204 (e.g., either toward or away from the second seal 212) will result in the second seal 212 being translated in a same manner (e.g., either toward or away from the first seal 210) in the second chamber 206.

In one implementation, the translation of the first seal 210 in the first chamber 204 can result in a substantially equivalent translation of the second seal 212 in the second chamber 206. As an example, if the first seal 210 is translated in a first direction a, a first distance b in the first chamber 204, the second seal 212 will be translated in the first direction a, a distance substantially equivalent to the first distance b in the second chamber 206. In this implementation, for example, the first seal 210 may be operably coupled 226 to the second seal 212 by a type of rigid assembly, such as bar, rod, wire, or otherwise direct-drive connector assembly that allows the two seals 210, 212 to move in concert with each other in the same direction and over the same relative distance.

In one implementation, the translation of the first seal 210 in the first chamber 204 may result in a proportional and non-equivalent translation of the second seal 212 in the second chamber 206. As an example, if the first seal 210 is translated in the first direction a, the first distance b in the first chamber 204, the second seal 212 may be translated in the first direction a, a second distance c in the second chamber 206, where c is substantially proportional to the first distance b, but where the second distance c is not equivalent to the first distance b. That is, the first distance b may be greater than or less than the second distance c, for example, where the relationship between the first distance b and the second distance c may be represented as a ratio b:c. In this implementation, for example, the first seal 210 may be operably coupled 226 to the second seal 212 by a type of non-rigid assembly, such as spring assembly, gear assembly, or otherwise non-direct drive connector that allows the two seals 210, 212 to move in the same direction, but at different relative translation rates.

In one implementation, the first chamber 204 and the second chamber 206 may comprise a substantially similar dimension, such as a diameter. For example, a diameter of the chamber body 202 may comprise a non-varying diameter barrel. In one implementation, the first seal 210 may be operably coupled 226 to the second seal 212 by a type of variable length link, further coupled with the actuator 228. For example, the variable length link can couple the first seal 210 and second seal 212 in the non-varying diameter barrel of the chamber body 202. In this example, using the actuator 228 to translate the first seal 210 in the first chamber 204 may result in a substantially proportional translation of the second seal 212 in the second chamber 206.

In one implementation, as illustrated in the example, 200 of FIG. 2, actuator 228 may be operably coupled with the first seal 210. The actuator 228 can be configured to apply a translation force to the first seal 210. As an example, the actuator 228 may be coupled with a user interface 250 (e.g., a grip, such as a thumb press) to which the user can apply the translation force (e.g., in or out). In this example, applying the translation force inward may result in the first seal 210 being translated toward the fluid port 208 (e.g., and therefore resulting in the second seal 212 translating forward). Further, applying the translation force to the actuator 228 outward (e.g., pulling the user interface 250) can result in the first seal 210 being translated away from the fluid port 208.

Figure 3A:
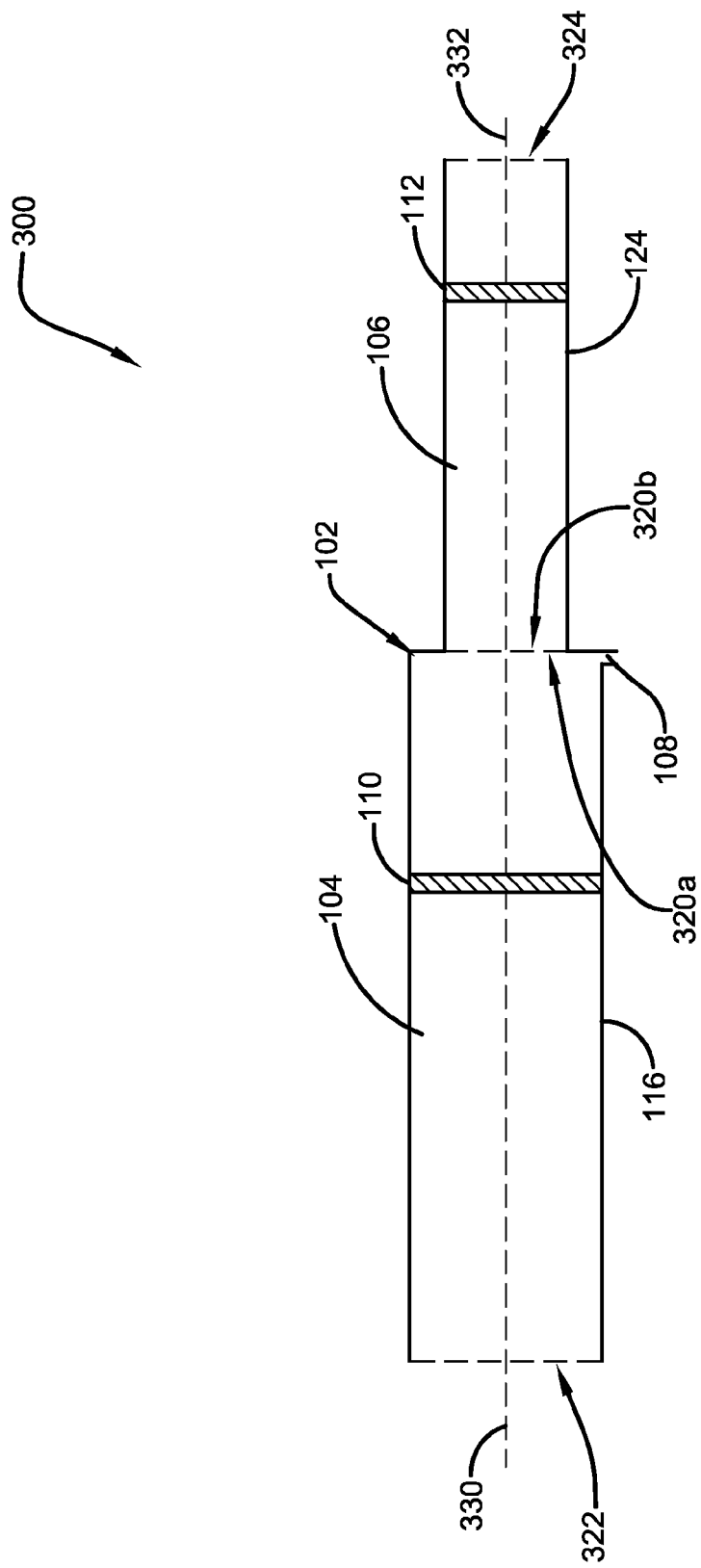

FIG. 3A is a component diagram illustrating an example implementation 300 of an apparatus for use with a syringe or pipette. With continued reference to FIGS. 1A, 1B and 2, in one implementation, as illustrated in FIG. 3A, the first seal 110 (e.g., 210 of FIG. 2) can be configured to slidably translate along a central, longitudinal axis 330 of the first chamber 104. Further, the second seal 112 (e.g., 212 of FIG. 2) can be configured to slidably translate along a central, longitudinal axis 332 of the second chamber 106.

In one implementation, as illustrated in FIG. 3A, the central, longitudinal axis 330 of the first chamber 104 may be axially aligned with the central, longitudinal axis 332 of the second chamber 106. In other implementations, the central, longitudinal axis 330 of the first chamber 104 may be aligned in parallel (e.g., geometrically) with the central, longitudinal axis 332 of the second chamber 106. In another implementation, the central, longitudinal axis 330 of the first chamber 104 may be aligned orthogonally to the central, longitudinal axis 332 of the second chamber 106.

FIGS. 3B-3E are component diagrams illustrating alternate example implementations 320, 340, 360, 380 of an apparatus for use with a syringe or pipette. In the example implementation 320 of FIG. 3B, the first chamber 104 is disposed adjacent to (e.g., parallel to) the second chamber 106 of the chamber body 102. In this implementation, for example, the first seal 110 and second seal 112 may be configured to translate in their respective chambers in opposite directions when fluid is displaced at the fluid port. Further, in this implementation, the second end 320a, 320b of the respective chambers can comprise an opening in a chamber wall between the respective chambers 104, 106, for example.

In another implementation 340, as illustrated in FIG. 3C, the first and second chambers 104, 106 may comprise a donut shape, for example, where a central portion of the respective chambers comprises a separate, central chamber 342 (e.g., of filled portion), that is not fluidly coupled with the first and second chambers 104, 106. In this implementation, for example, a varying-sized central chamber 342 may be configured to allow the second chamber 106 to have a smaller volume than the first chamber 104. Further, in this implementation the first and second seals 110, 112 can be configured to accommodate the central chamber 342, for example, by comprising donut-shaped configuration. FIG. 3D illustrates another example implementation 360, where the chamber body comprises an alternate central chamber 362 design. In this implementation, the chamber body 102 and the alternate central chamber 362 comprise a varied width (e.g., diameter), thereby accommodating a different volume for the first and second chamber 104, 106.

FIG. 3E comprises another example implementation 380, where the width (e.g., diameter) of the chamber body 102 constantly decreases from the first end 322 of the first chamber 104 to the first end 324 of the second chamber 106. As an illustrative example, in this implementation, the chamber body may comprise a frustoconical shape. Further, in this implementation, the first seal 110 and the second seal 112 may respectively be configured to deform (e.g., contract and expand) in a manner that allows them to continue to provide a fluid seal when translating along the constantly decreases width of the chamber body 102. In one implementation, a variable length linked coupling (e.g., described above in FIG. 2) may be disposed in the chamber body 102 that comprises constantly decreasing diameter. Further, in one or more implementations, the variable length linked coupling, or a rigidly linked coupling (e.g., described above in FIG. 2) may be implemented in any of the example implementations described herein.

It will be appreciated that the apparatuses, devices, and methods, described herein, are merely limited to the example implementations described herein. It is anticipated that those skilled in the art may devise alternate arrangements and shapes for the chambers and chamber bodies, etc. For example, the chamber body (e.g., in cross-section) may comprise a circle, oval, square, rectangle, triangle, or some other polygon shape configured to provide a desired operation. Further, for example, the first and second chambers 104, 106 may be arranged in a variety of ways, such as sequentially, in parallel (e.g., geometrically), one inside the other, etc. Additionally, in one implementation, the first and second chamber 104, 106 may respectively comprise different diameters geometries. For example, the first chamber 104 may comprise a first diameter geometry (e.g., round) and the second chamber 106 may comprise a second diameter geometry (e.g., donut-shaped).

As illustrated in FIG. 3A, the first chamber 104 can comprise at least a first chamber wall 116, a first end 322, and a second end 320a. In one implementation, the first end 322 can comprise an opening to the outside of the chamber body 102. As an example, the first end 322 of the first chamber 104 may comprise an opening that comprises a fluid communication between the inside of the first chamber 104 and the outside of the chamber body 102, such that a fluid may pass from the first chamber 104 to the outside. As an illustrative example, as illustrated in FIG. 3A, if the first seal 110 is slidably translated toward the first end 322, and the space between the first seal 110 and the first end 322 comprised a fluid gas (e.g., air), the fluid gas may be displaced from inside the first chamber 104 to the outside at the first end 322.

In one implementation, the second end 320a of the first chamber 104 can comprise an opening in fluid communication with the second chamber 106. Further, the second chamber 106 can comprise at least a second chamber wall 124, a first end 324, and a second end 320b. In one implementation, the second end 320b may comprise an opening that is in fluid communication with the first chamber 104. That is, for example, the second end 320a of the first chamber 104 may be adjacent to (e.g., and congruent with) the second end 320b of the second chamber 106.

As an illustrative example, as illustrated in FIG. 3A, if the first seal 110 is slidably translated toward the second end 320a, and the space between the first seal 110 and the second end 320a comprised a fluid (e.g., gas such as air; or fluid liquid), at least a portion of the fluid may be displaced from the first chamber 104, through opening at the second end 320a/320b, into the second chamber 106 (e.g., and another portion of fluid may be displaced out of the chamber body 102 through the fluid port 108). As another example, if the first seal 110 is slidably translated toward the first end 322, thereby resulting in the second seal to be translated toward its second end 320b, fluid disposed in the second chamber, between the second seal 112 and the second end 320b, may be displaced from the second chamber 106, through opening at the second end 320b/320a, into the first chamber 104 (e.g., and fluid may be displaced into the first chamber 104 from outside the chamber body 102 through the fluid port 108).

It will be appreciated that, while particular implementations have been illustrated and described, herein, the shape, size and/or dimensions of the exemplary pipette or syringe may not be limited to these example implementations. For example, the fluid port may be implemented in a variety of locations and having various dimensions, comprising various diameters, shapes, and/or lengths. Several example implementations are described below. As an example, the fluid port may comprise a connection means that allows the fluid port to be operably coupled with a device for use in transfer and/or injection of fluids. As another example, the fluid port may be coupled with an elongated tube used to visually observe an amount of fluid displaced through the fluid port.

In one implementation, the first end 324 of the second chamber 106 can comprise an opening to the outside of the chamber body 102. As an example, the first end 324 of the second chamber 106 may comprise an opening that comprises a fluid communication between the inside of the second chamber 106 and the outside of the chamber body 102, such that a fluid may pass from the second chamber 106 to the outside. As an illustrative example, as illustrated in FIG. 3A, if the second seal 112 is slidably translated toward the first end 324, and the space between the second seal 112 and the first end 324 comprised a fluid gas (e.g., air), the fluid gas may be displaced from inside the second chamber 106 to the outside of the chamber body 102, at the first end 324.

Figure 4A:
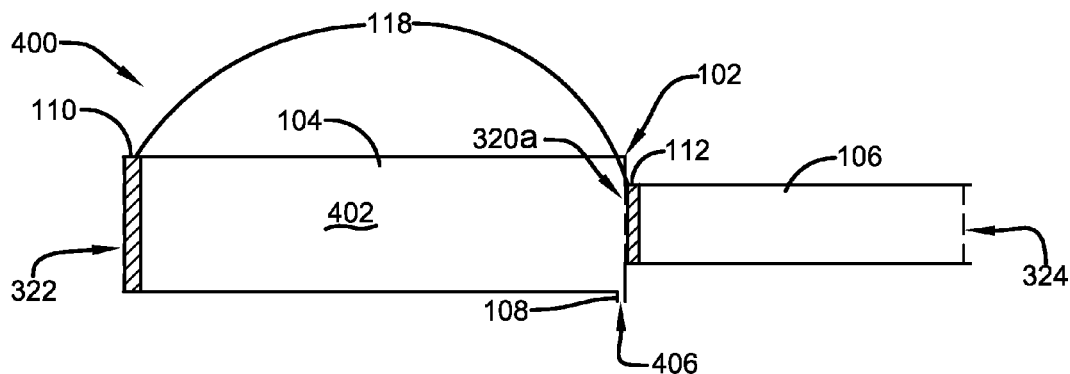
FIGS. 4A, 4B and 4C are component diagrams illustrating example implementations of an apparatus for use with a syringe or pipette.
Figure 4B:
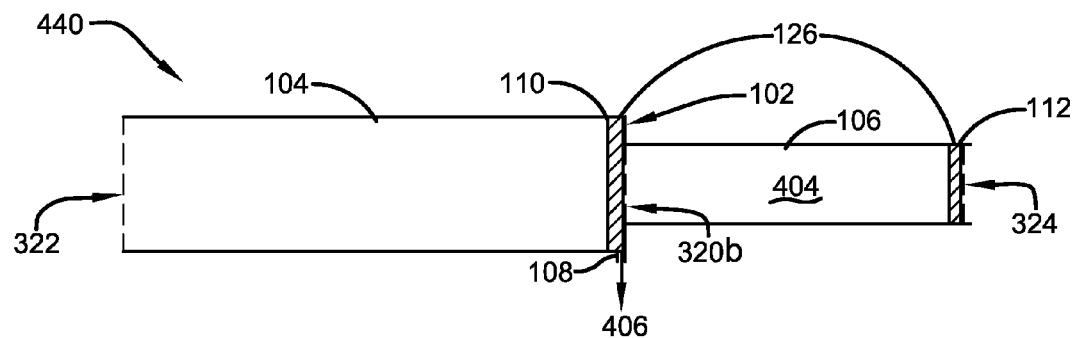
Figure 4C:
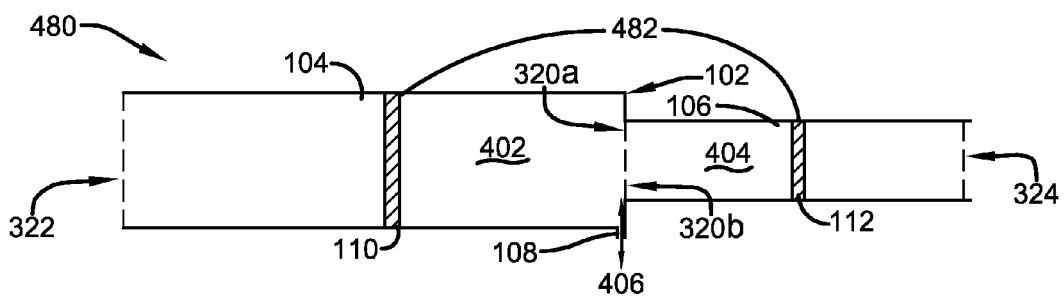

FIGS. 4A-4C are component diagrams illustrating example implementations 400, 440, 480 of an apparatus for use with a syringe or pipette. With continued reference to FIGS. 1A, 1B, 2, and 3A-3E, in one implementation, as illustrated in FIGS. 4A and 4B, the first position 118 of the first seal 110 and the second seal 112 can comprise the first seal 110 disposed at the first end 322 of the first chamber 104, and the second seal 112 disposed at the second end 320b of the second chamber 106. Further, in one implementation, the second position 126 of the first seal 110 and the second seal 112 can comprise the first seal 110 disposed at the second end 320a of the first chamber 104, and the second seal 112 disposed at the first end 324 of the second chamber 106.

As illustrated in FIGS. 4A-4C, in one implementation, the first chamber 104 comprising a fourth volume 402 defined by the first seal 110 and the second end 320a of the first chamber 104. Further, the second chamber 106 can comprise a fifth volume 404 defined by the second seal 112 and the first end 324 of a second chamber 106. Additionally, the fluid port 108 can be configured to transfer a sixth volume 406 between the inside of the chamber body 102 and the outside of the chamber body 102. In one implementation, the first volume 114 is substantially equivalent to the sum of the fourth volume 402, the fifth volume 404 and the sixth volume 406, during translation of the first seal 110 and second seal 112.

As an illustrative example, the first volume 114, as illustrated in FIG. 1A, is substantially equivalent to the fourth volume 402, as illustrated in FIG. 4A, when the first seal 110 and second seal 112 are disposed in the first position 118. Therefore, in this example, the fifth volume 404 and sixth volume 406 may respectively comprise zero. Alternately, when the first seal 110 and second seal 112 are disposed in the second position, as illustrated in FIG. 4B (e.g., and FIG. 1B), the fourth volume 402 may comprise zero, and the first volume 114 may be substantially equivalent to the sum of the fifth volume 404 and the sixth volume 406. Further, the first and second seal 110, 112 may be disposed in a third position 482, comprising a position between the first position 118 and the second position 126.

That is, in the example 440 of FIG. 4B, the amount of fluid displaced (e.g., 406) from inside the chamber body 102 to outside, via the fluid port 108, may comprise the difference between the fourth volume 402 (from example, 400) and the fifth volume 404 (from example 440). However, in the example 480 of FIG. 4C, the amount of fluid displaced from inside the chamber body 102 to outside, via the fluid port 108, may comprise the difference between the first volume 114 and the sum of fourth volume 402 and the fifth volume 404.

In one implementation, the volume difference between the fourth and fifth volumes 402, 404, can be dictated by a size of the respective first and second chambers 104, 106. This difference, for example, can dictate the amount of fluid displaced at the fluid port 108. In one implementation, the ratio of the first volume 114 to the third volume 122 (e.g., displaced at the fluid port) can comprise ten to one or greater (>10:1), one hundred to one or greater (>100:1), one-thousand to one or greater (>1,000:1), or ten-thousand to one or greater (>10,000:1) (e.g., or some other ratio). As an example, a syringe and/or pipette may be devised that can displace (e.g., draw and/or discharge) in a granularity of microliters (μl), while the chamber body (e.g., 102) may displace in a granularity of milliliters (ml) (e.g., between the first and second chambers 104, 106).

As an illustrative example, the chamber body (e.g., 102) of the syringe and/or pipette may comprise a first chamber (e.g., 104) configured to hold a fourth volume (e.g., 402) of 10 ml, and second chamber (e.g., 106) configured to hold the fifth volume (e.g., 404) of 9.99 ml, which would result in a sixth volume (e.g., 406) of 10 μl. In this example, translating the first seal (e.g., 110) from the first end (e.g., 322) of the first chamber to the second end (e.g., 320a) of the first chamber (e.g., and therefore resulting in the translation of the second seal (e.g., 112) from the second end (e.g., 324) of the second chamber to the second end (e.g., 320b) of the second chamber) would result in 10 μl being displaced (e.g., discharged) from the first chamber to the outside of the chamber body at the fluid port (e.g., 108). Conversely, translating the first seal from the second end of the first chamber to the first end of the first chamber (e.g., and therefore resulting in the translation of the second seal from the first end of the second chamber to the second end of the second chamber) would result in 10 μl being displaced (e.g., drawn) into the first chamber from the outside of the chamber body at the fluid port.

A syringe or pipette may be devised that that can be used to transfer a low volume (e.g., ultra-low volume) of fluid when compared with an amount of fluid internally displaced by actuation of the syringe or pipette. That is, for example, a user of the syringe or pipette may be able to apply a force vector to an actuator that is typical of a large volume transfer, but it result in merely a low volume transfer (e.g., collection or dispersal) of the fluid (e.g., liquid, gas, plasma).

Figure 5A:
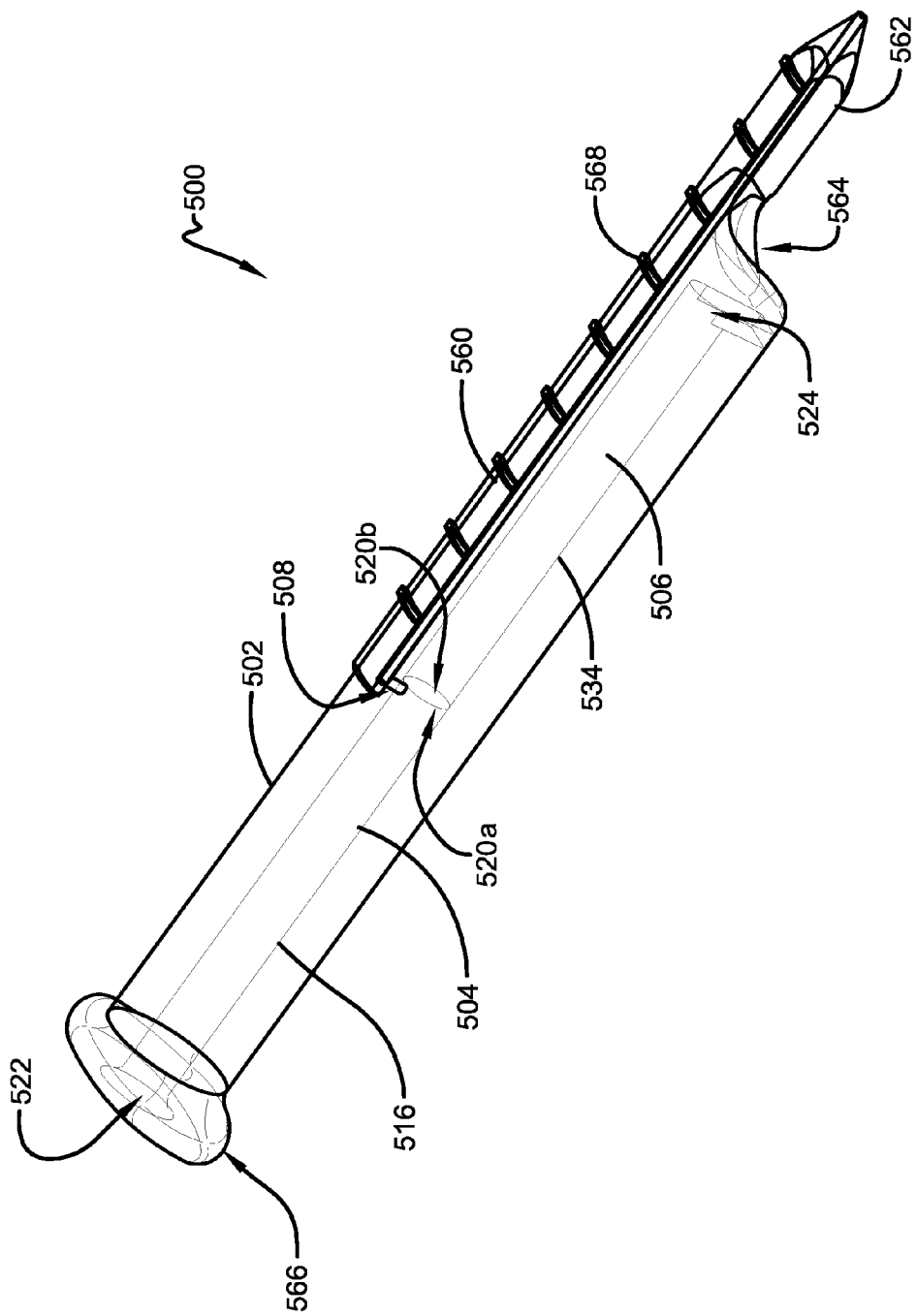
FIG. 5A is a perspective illustration of at least a portion of an example pipette device, which comprises one or more portions the systems described herein.
Figure 5B:
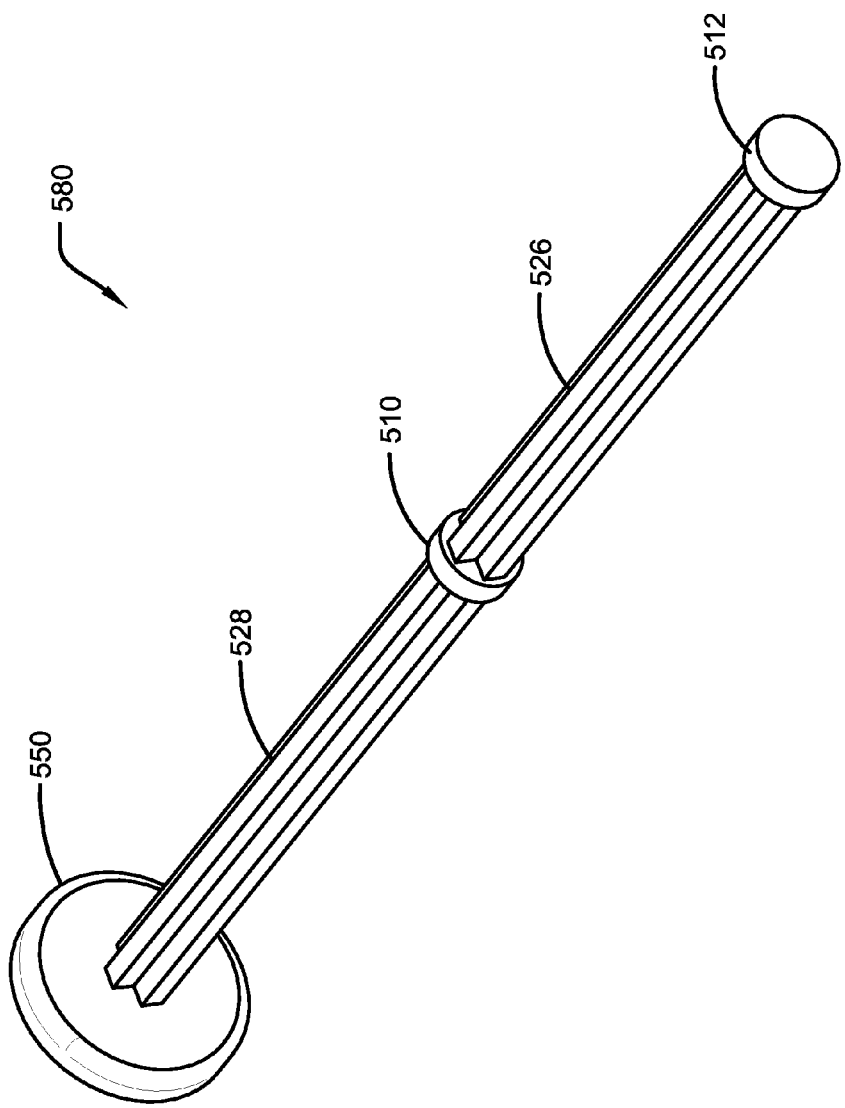
FIG. 5B is a perspective illustration of at least a portion of an example pipette device, which comprises one or more portions the systems described herein.
Figure 6:
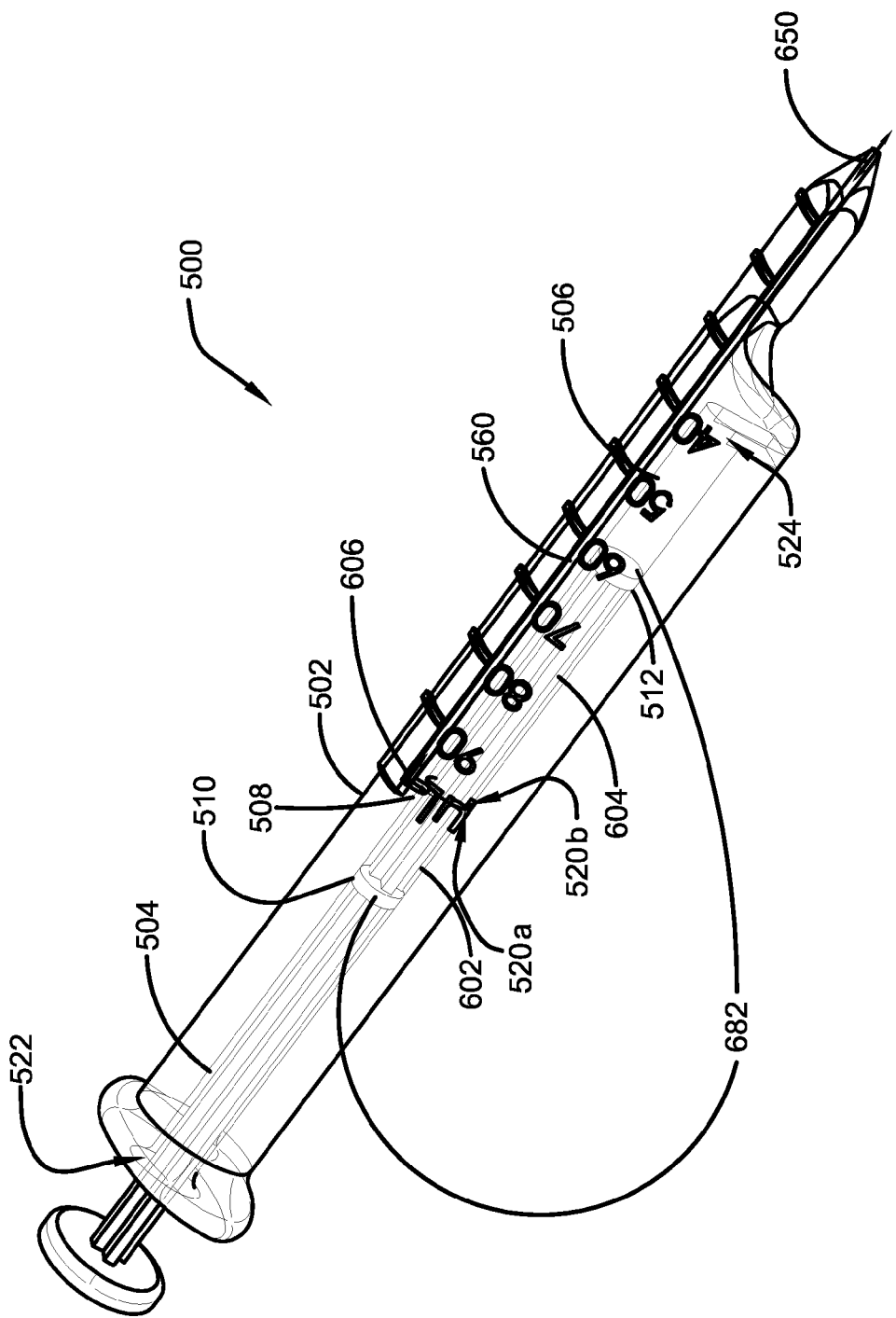
FIG. 6 is a perspective illustration of one or more portions of an example pipette device, which comprises one or more portions the systems described herein.

FIGS. 5A, 5B and 6 are perspective illustrations of one or more portion of an example pipette device 500, which comprise one or more portions the systems described herein. In this example implementation 500, in FIG. 5A, a first chamber 504 (e.g., 104 of FIG. 1) and second chamber 506 (e.g., 106 of FIG. 1) are comprised in a chamber body 502 (e.g., 102 of FIG. 1). The first chamber comprises a first chamber wall 516, a first end 522, and a second end 520a. The second chamber 506 comprise a second chamber wall 534, a first end 524, and a second end 520b, where, the second chamber 506 is in fluid communication with the first chamber 504. Further, the example pipette device 500 comprises a fluid port 508 (e.g., 108 of FIG. 1) that is disposed in fluid communication with the first chamber 504 and the outside of the first and second chambers 504, 506.

In FIG. 5B, an example device 580 comprises a first seal 510 and a second seal 512. As illustrated in FIG. 6, the first seal 510 can be disposed in the first chamber 504, and may be configured to provide a fluid seal between the first end 522 and the second end 520a of the first chamber 504. Further, the first seal 510 can be configured to translate between the first end 522 and the second end 520a of the first chamber 504 to facilitate displacing fluid from the first chamber 504. As shown in FIG. 6, the second seal 512 can be disposed in the second chamber 506, and may be configured to provide a fluid seal between the first end 524 and the second end 520b of the second chamber 506. Additionally, the second seal 512 can be configured to translate between the first end 524 and the second end 520b of the second chamber 506 to facilitate displacing fluid from the second chamber 506.

In one implementation, the first seal 510 can be configured to facilitate displacement of fluid (e.g., gas, such as air, liquid, or plasma) from the first chamber 504 and into the second chamber 506 and/or the fluid port 508. Further, the first seal 510 can be configured to facilitate replacement of fluid into the first chamber 504 from the second chamber 506 and/or the fluid port 508. That is, for example, the first chamber 504 may comprise a first volume of fluid 602 disposed between the first seal 510 and the second end 520a of the first chamber 504.

In this example, when the first seal 510 is translated from the first end 522 toward the second end 520a, the first volume of fluid 602 may be displaced into the second chamber 506 and the fluid port 508; resulting in a second volume of fluid 604 in the second chamber 506, and a third volume of fluid 606 at the fluid port 508. Further, in this example, the amount of fluid displaced from the first chamber 504 (e.g., the first volume of fluid 602) may be substantially equivalent to the second volume of fluid 604 and the third volume of fluid 606.

As another example, when the first seal 510 is translated from the second end 520a toward the first end 522, the second volume of fluid 604 may be displaced into the first chamber 504 from the second chamber, and the third volume of fluid 606 may be displaced from the fluid port 508. This can result in the first volume of fluid 602 in the first chamber 504. Further, in this example, the amount of fluid displaced into the first chamber 504 (e.g., the first volume of fluid 602) may be substantially equivalent to the second volume of fluid 604 from the second chamber 506 and the third volume of fluid 606 from the fluid port 508. In one implementation, the third volume of fluid 606, displaced at the fluid port 508, upon translation of the first seal 510 in the first chamber 504 may be substantially equivalent to the difference between the sum of the first volume of fluid 602 and second volume of fluid 604, when the first seal 510 is disposed at the second end 520a, and the sum of the first volume of fluid 602 and second volume of fluid 604, when the first seal 510 is disposed at the first end 522.

As illustrated in FIGS. 5B and 6, the first seal 510 can be operably coupled 526 with the second seal 512. The coupling 526 between the first seal 510 and the second seal 512 can be configured to facilitate in translation of the second seal 512 at a substantially similar rate as a translation of the first seal 510. That is, for example, when an actuator 528, which is operably coupled with the first seal 510, is activated by applying a translation force, such as at an activator grip 550, the translation force is applied to the first seal 510. In this example, the translation force applied to the first seal may result in a translation force being applied to the coupling 526. This, in-turn, can apply a translation force to the second seal 512 at a substantially similar rate, resulting in the first and second seals 510, 512 being translated in their respective chambers 504, 506 at substantially similar rate. In another implementation, the coupling 526 between the first seal 510 and the second seal 512 may be configured to facilitate translation of the second seal 512 at a rate proportional to the rate of translation of the first seal 510.

Further, as illustrated in FIGS. 5A, 5B and 6, the second end 520b of the second chamber 506 comprise an opening in fluid communication with an opening in the second end 520a of the first chamber 504. Further, the first end 522 of the first chamber 504 can comprise an opening in fluid communication with the outside of the first chamber 504. Additionally, the first end 524 of the second chamber 506 can comprise an opening in fluid communication with the outside of the second chamber 506.

In one implementation, as illustrated in FIG. 6, the fluid port 508 can be configured to be fluidly coupled with a graduated chamber 560, where the graduated chamber 560 can be configured to hold fluid in a visually demarcated position 568. For example, the exemplary pipette device 500 can be configured to draw fluid 650 (e.g., a desired target liquid) into the graduated chamber 560, such as by drawing the grip 550, which, in-turn, can translate the first seal 510 and second seal 512, drawing the third volume of fluid 606 across the fluid port 508 and into the first chamber 504. In this example, the amount of fluid drawn into the pipette 650 may be substantially equivalent to the third volume of fluid 606. The volume of fluid drawn into the pipette 650 can be visually observed in the graduated chamber 560, for example.

In one implementation, a volume comprised in the graduated chamber 560 may be substantially equivalent to (e.g., or greater than) the third volume of fluid 606 translated across the fluid port 508. For example, the difference between the volume displaced at the first chamber 504 and the volume displace at the second chamber 506, when the first seal 510 and second seal 512 are translated in the respective chambers, should be less than or equal to the volume comprised in the graduated chamber 560. In this way, for example, a fluid transferred or by the pipette or syringe device may not be displaced into the interior of the chamber body 502. As another example, where the third volume 606 is one hundred microliters (100 µl) the volume of the graduated chamber 560 should be greater than or equal to $\pi^2 \times$length of the graduated chamber 560.

In one implementation, as illustrated in FIGS. 5A, 5B and 6, the example pipette device 500 may comprise user interface features 564, 566, which may be configured to allow a user to appropriately grip the pipette device 500 during use. For example, one or more of a user's fingers or other portions of the user's hand may be placed at the user interface features 564, 566, which may allow for an ergonomic use of the device.

Figure 7:
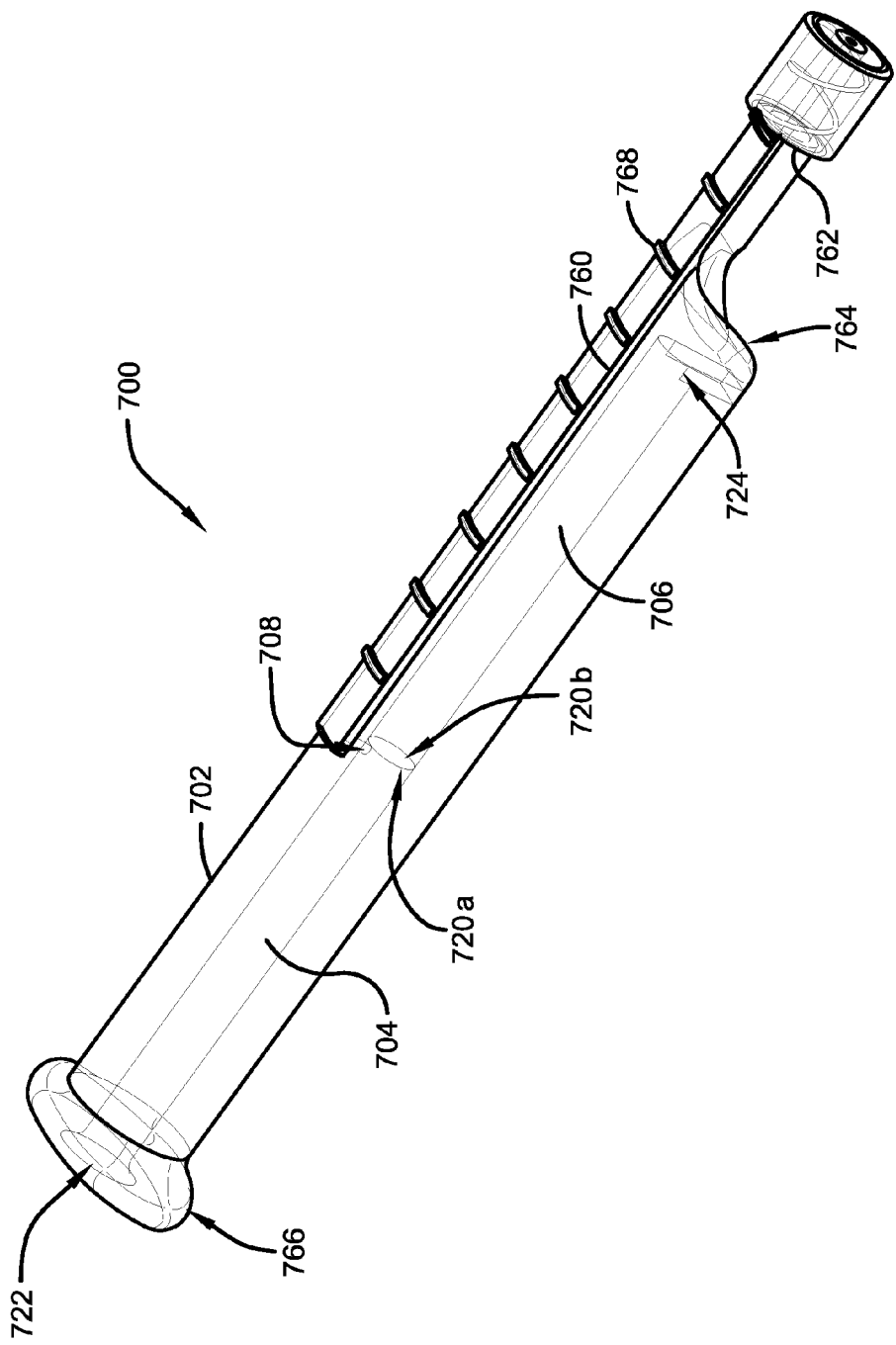
FIG. 7 is a perspective illustration of at least a portion of an example syringe device, which comprises one or more portions the systems described herein.
Figure 8:
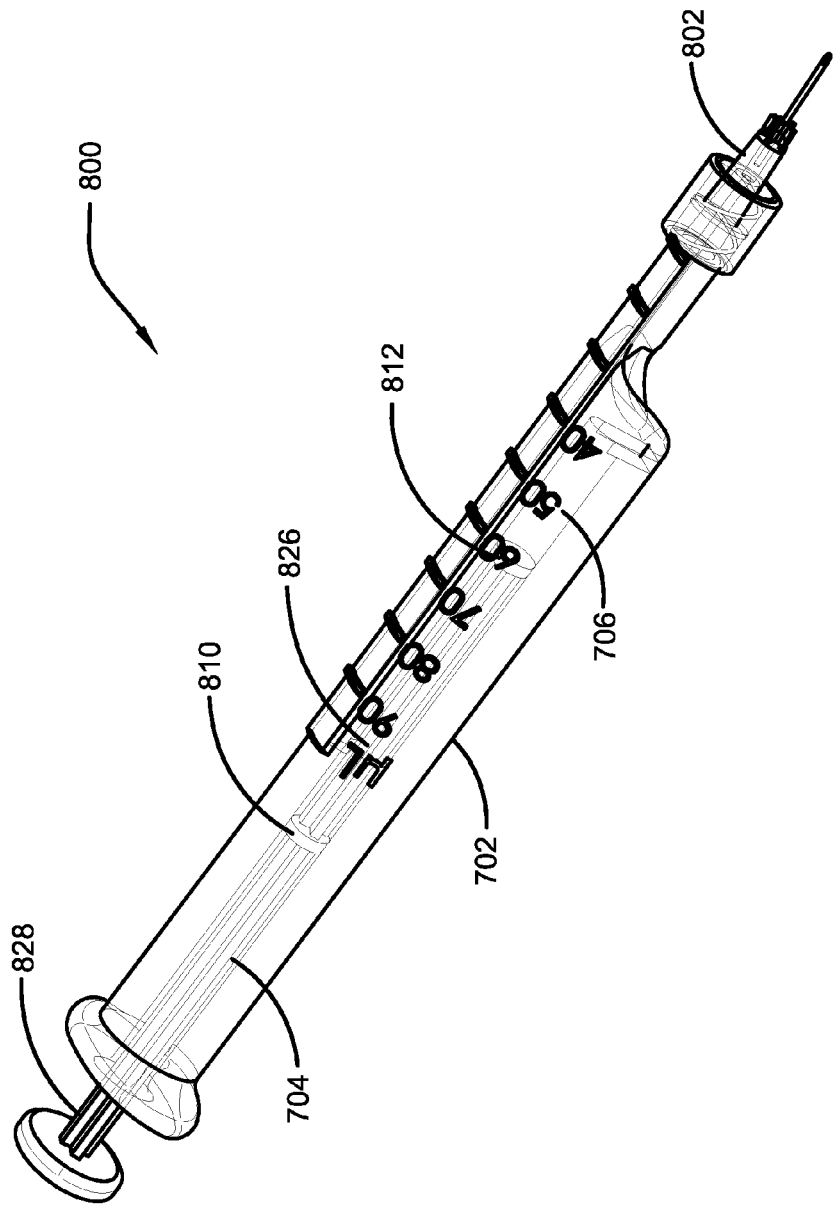
FIG. 8 is a perspective illustration of one or more portions of an example syringe device, which comprises one or more portions the systems described herein.

FIGS. 7 and 8 are perspective illustrations of one or more portion of an example syringe device 700, which comprise one or more portions the systems described herein. The example, syringe device 700 comprises a chamber body 702, a first chamber 704, and a second chamber 706. The first chamber 704 comprises a first end 722 and a second end 720a in fluid communication with a second end 720b of the second chamber 706, which further comprises a first end 724. The example, syringe device 700 can further comprise a fluid port 708 in fluid communication with the first chamber 704. The first end 722 of the first chamber 704 is in fluid communication with the outside of the chamber body 702; and the first end 724 of the second chamber 706 is in fluid communication with the outside of the chamber body 702.

In one implementation, the example, syringe device can comprise a graduated chamber 760 in fluid communication with the fluid port 708. The graduated chamber 760 may comprise graduation marks 768 configured to provide a visually guide for a volume of fluid disposed in the graduated chamber 760. In this implementation, the example, syringe device 700 can comprise a needle receiving component 762, configured to operably couple with a syringe needle module 802, for example, to provide a seal between the graduated chamber 760 and a needle. In one implementation, the needle receiving component 762 can comprise an appropriate coupling means for any type of needle or injection device, and is not limited to that depicted in FIG. 7. Further, in one implementation, the syringe device may comprise a fixed needle or injection device, for example, which is fixedly coupled with the syringe device.

As illustrated in FIG. 8, the example syringe device can comprise a first seal 810, disposed in the first chamber 704, and a second seal 812, disposed in the second chamber 706. Further, in one implementation, as illustrated in FIGS. 7 and 8, the example, syringe device 700 may comprise user interface features 764, 766, configured to facilitate use of the syringe device 700 by a user. Additionally, the first and second seals 810, 812 may be operably coupled by a coupler 826; and the first seal may be operably coupled with an actuator 828, configured to apply a translation force to the first seal 810, which in-turn may result in a translation force applied to the second seal 812, via the coupler 826.

A method may devised for transferring a low volume of fluid, using a syringe or pipette, such by using one or more of the apparatus, devices, syringes and/or pipettes described herein. That is, for example, a user may be able use an example pipette or syringe, using an amount of force and over a period of time that is typical of a large volume transfer, but it resulting in merely a low volume transfer of the fluid. As an example, the user may be able to apply an amount of force over a period of time equivalent to drawing or displacing ten milliliters, however, they may be merely drawing or displacing 10 microliters.

Figure 9:
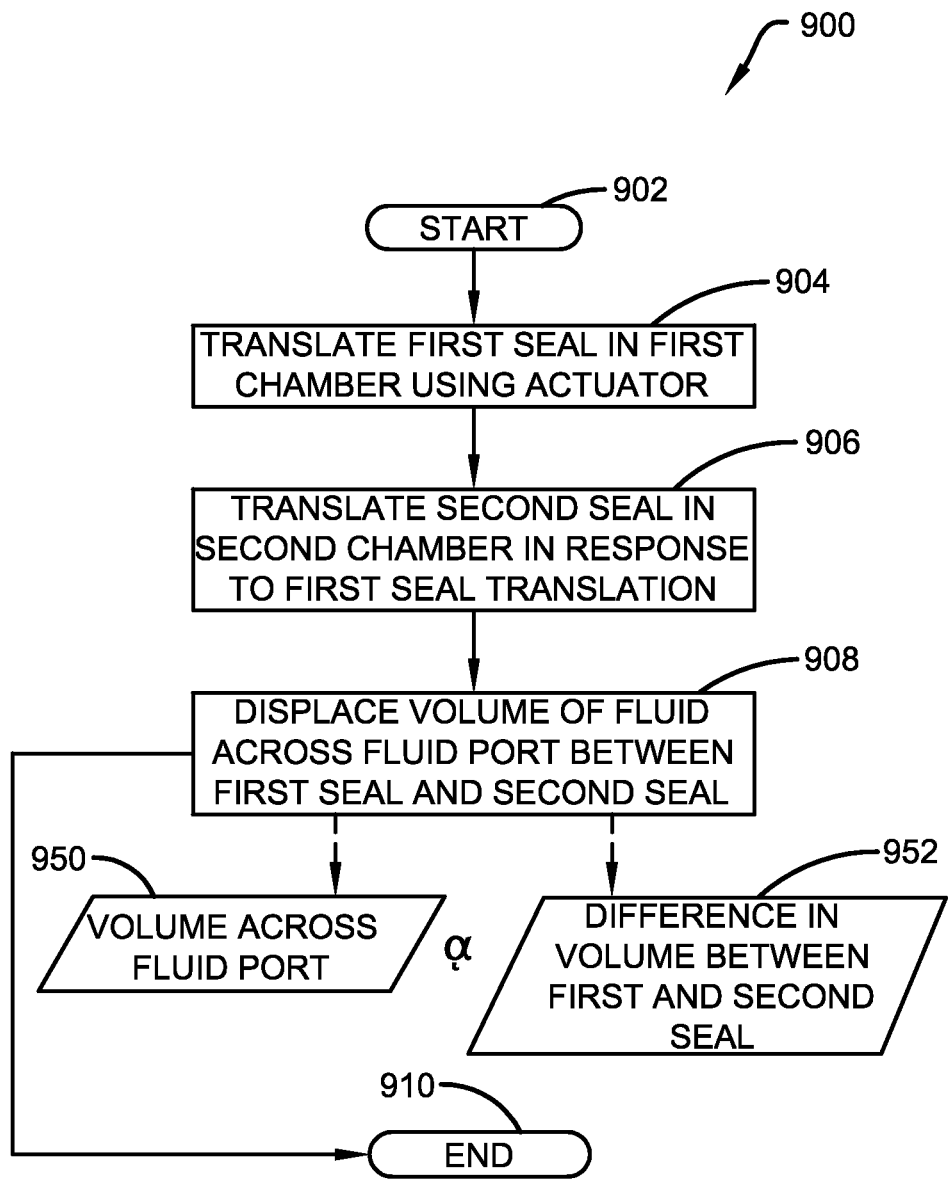
FIG. 9 is a flow diagram illustrating an exemplary method for transferring a low volume of fluid, using a syringe or pipette.

FIG. 9 is a flow diagram illustrating an exemplary method 900 for transferring a low volume of fluid, using a syringe or pipette. The exemplary method 900 begins at 902. At 904, a first seal is translated in a first chamber of a chamber body using an actuator that applies a translation force to the seal. At 906, a second seal is translated in a second chamber of the chamber body. In this implementation, the second chamber is in fluid communication with the first chamber, and the second seal is translated in response to the translation of the first seal.

At 908, as a result of the translation of the first and second seals, a volume of fluid 950 is displaced across a fluid port that can be disposed between the first seal and the second seal in the chamber body. In this implementation, the volume of fluid displaced 950 is substantially equivalent to a difference between a first volume and a second volume 952, where the first volume can be defined by an interior wall of the chamber body wall, the first seal and the second seal when the first seal and second seal are disposed in a first position. Further, the second volume can be defined by an interior wall of the chamber body wall, the first seal and the second seal when the first seal and second seal are disposed in a second position.

As an example, when the first seal is disposed at the first end of the first chamber, and the second seal is disposed at the second end of the second chamber, the first volume may comprise substantially all of the volume of the second chamber. Further, in this example, when the first seal is disposed at the second end of the first chamber, and the second seal is disposed at the first end of the second chamber, the second volume may comprise substantially all of the volume of the second chamber. Additionally, the first volume may be larger than the second volume, for example, where the first volume may comprise one or more milliliters and the second volume may be less than the first volume by one or more microliters. In this way, for example, the third volume may comprise one or more microliters. In one implementation, the volume of fluid displaced 950 across the fluid port may be less than or equal to one tenth of the first volume; less than or equal to one hundredth of the first volume; less than or equal to one, one thousandth of the first volume; or less than or equal to one, ten thousandth of the first volume (e.g., or some other ratio).

The word "exemplary" is used herein to mean serving as an example, instance or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, at least one of A and B and/or the like generally means A or B or both A and B. In addition, the articles "a" and "an" as used in this application and the appended claims may generally be construed to mean "one or more" unless specified otherwise or clear from context to be directed to a singular form.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. Reference throughout this specification to "one implementation" or "an implementation" means that a particular feature, structure, or characteristic described in connection with the implementation is included in at least one implementation. Thus, the appearances of the phrases "in one implementation" or "in an implementation" in various places throughout this specification are not necessarily all referring to the same implementation. Furthermore, the particular features, structures, or characteristics may be combined in any suitable manner in one or more implementations. Of course, those skilled in the art will recognize many modifications may be made to this configuration without departing from the scope or spirit of the claimed subject matter.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure.

In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

What is claimed is:

1. An apparatus for use as part of a syringe or pipette, comprising:
    a chamber body comprising a first chamber, a second chamber, and a fluid port;
    a first seal disposed in the first chamber; and
    a second seal disposed in the second chamber;
    the chamber body comprising a first volume defined by:
        at least a first chamber wall, the first seal, and the second seal, when the first seal and second seal are disposed in a first position, respectively; and
        a sum of: a second volume defined by at least a second chamber wall, the first seal, the second seal; and a third volume comprising fluid displaced at the fluid port, when the first seal and second seal are disposed in a second position, respectively.

2. The apparatus of claim 1, the first seal operably coupled with the second seal, such that the second seal is translated in the second chamber in proportion to a translation of the first seal in the first chamber.

3. The apparatus of claim 2:
    the translation of the first seal in the first chamber results in a substantially equivalent translation of the second seal in the second chamber; or
    the translation of the first seal in the first chamber results in a proportional and non-equivalent translation of the second seal in the second chamber.

4. The apparatus of claim 1, comprising an actuator operably coupled with the first seal, and configured to apply a translation force to the first seal.

5. The apparatus of claim 1, one or more of:
    the first chamber comprising the first chamber wall, a first end, and a second end, and one or more of:
        the first end comprising an opening to the outside of the chamber body; and
        the second end comprising an opening in fluid communication with the second chamber; and
    the second chamber comprising at the second chamber wall, a first end, and a second end, and one or more of:
        the first end comprising an opening to the outside of the chamber body; and
        the second end comprising an opening in fluid communication with the first chamber.

6. The apparatus of claim 5,
    the first position comprising the first seal disposed at the first end of the first chamber, and the second seal disposed at the second end of the second chamber; and
    the second position comprising the first seal disposed at the second end of the first chamber, and the second seal disposed at the first end of the second chamber.

7. The apparatus of claim 1:
    the first chamber comprising a fourth volume defined by the first seal and a second end of the first chamber;
    the second chamber comprising a fifth volume defined by the second seal and a second end of a second chamber; and
    the fluid port is configured to transfer a sixth volume between the inside of the chamber body and the outside of the chamber body.

8. The apparatus of claim 7, the first volume is substantially equivalent to the sum of the fourth volume, the fifth volume and the sixth volume, during translation of the first seal and second seal.

9. The apparatus of claim 1, a ratio of the first volume to the third volume comprising:
    ten to one or greater;
    one hundred to one or greater;
    one-thousand to one or greater; or
    ten-thousand to one or greater.

10. A syringe or pipette device, comprising:
    a first chamber, comprising a first chamber wall, a first end, and a second end;
    a second chamber, comprising a second chamber wall, a first end, and a second end, the second chamber in fluid communication with the first chamber;
    a first seal, disposed in the first chamber, and configured to:
        provide a fluid seal between the first end and the second end of the first chamber; and
        translate between the first end and the second end of the first chamber to facilitate displacing fluid from the first chamber;
    a second seal disposed in the second chamber, the second seal configured to:
        provide a fluid seal between the first end and the second end of the second chamber; and
        translate between the first end and the second end of the second chamber to facilitate displacing fluid from the second chamber; and
    a fluid port disposed between the first seal and the second seal, the fluid port in fluid communication with the first chamber and the outside of the first and second chambers.

11. The device of claim 10, the first seal configured to perform one or more of:
    facilitate displacement of fluid from the first chamber and into one or more of: the second chamber, and a fluid port; and
    facilitate replacement of fluid into the first chamber from one or more of: the second chamber, and the fluid port.

12. The device of claim 10, the first seal operably coupled with the second seal, the coupling configured to facilitate one of:
    translation of the second seal at a substantially similar rate as a translation of the first seal; and
    translation of the second seal at a rate proportional to the rate of translation of the first seal.

13. The device of claim 10, the second end of the second chamber comprising an opening in fluid communication with an opening in the second end of the first chamber.

14. The device of claim 10, one or more of:
    the first end of the first chamber comprising an opening in fluid communication with the outside of the first chamber; and
    the first end of the second chamber comprising an opening in fluid communication with the outside of the second chamber.

15. The device of claim 10, the fluid port configured to be fluidly coupled with a graduated chamber, the graduated chamber configured to hold fluid in a visually demarcated position.

16. The device of claim 10, comprising an actuator operably coupled with the first seal, and configured to apply a translation force to the first seal.

17. The device of claim 10,
- the first chamber configured to hold a first volume between the second end and the first seal; and
- the second chamber configured to hold a second volume between the second end and the second seal.

18. The device of claim 17, a volume of fluid displaced at the fluid port upon translation of the first seal in the first chamber is substantially equivalent to the difference between the sum of the first volume and second volume, when the first seal is disposed at the second end, and the sum of the first volume and second volume, when the first seal is disposed at the first end.

19. A method for transferring a low volume of fluid, using a syringe or pipette, comprising:
- translating a first seal in a first chamber of a chamber body using an actuator that applies a translation force to the first seal;
- translating a second seal in a second chamber of the chamber body, the second chamber in fluid communication with the first chamber, the second seal translated in response to the translation of the first seal; and
- displacing a volume of fluid across a fluid port, disposed between the first seal and the second seal in the chamber body, the volume of fluid substantially equivalent to a difference between a first volume and a second volume;
  - the first volume defined by an interior wall of the chamber body, the first seal and the second seal when the first seal and second seal are disposed in a first position; and
  - the second volume defined by an interior wall of the chamber body, the first seal and the second seal when the first seal and second seal are disposed in a second position.

20. The method of claim 19, the volume of fluid displaced across the fluid port is:
- less than or equal to one tenth of the first volume;
- less than or equal to one hundredth of the first volume;
- less than or equal to one, one thousandth of the first volume; or
- less than or equal to one, ten thousandth of the first volume.

* * * * *